(12) United States Patent
Ellson

(10) Patent No.: US 9,192,932 B2
(45) Date of Patent: Nov. 24, 2015

(54) CLOSURES WHICH CONTAIN RESERVOIRS AND ALLOW ACOUSTIC EJECTION

(75) Inventor: Richard N. Ellson, Palo Alto, CA (US)

(73) Assignee: LABCYTE INC., Sunnyvale, CA (US)

( * ) Notice: Subject to any disclaimer, the term of this patent is extended or adjusted under 35 U.S.C. 154(b) by 1599 days.

(21) Appl. No.: 12/143,252

(22) Filed: Jun. 20, 2008

(65) Prior Publication Data

US 2009/0019956 A1 Jan. 22, 2009

Related U.S. Application Data

(60) Provisional application No. 60/936,586, filed on Jun. 20, 2007.

(51) Int. Cl.
- *G01N 1/10* (2006.01)
- *G01N 1/00* (2006.01)
- *B01L 3/02* (2006.01)
- *G01N 1/02* (2006.01)

(52) U.S. Cl.
CPC ....... *B01L 3/0268* (2013.01); *B01L 2200/0642* (2013.01); *B01L 2300/046* (2013.01); *B01L 2300/0829* (2013.01); *B01L 2300/0851* (2013.01); *B01L 2400/0439* (2013.01); *G01N 1/00* (2013.01); *G01N 1/02* (2013.01); *G01N 1/10* (2013.01)

(58) Field of Classification Search
CPC ....... B01L 3/0268; B01L 3/0241; B01L 3/02; B01L 3/00; B01L 22/0642; B01L 2200/06; B01L 2200/00; B01L 2400/04; B01L 2400/00; G01N 1/10; G01N 1/02; G01N 1/00
USPC .................. 422/553, 552, 551, 547, 500, 50; 73/864.63, 864.51, 864, 864.91, 863
See application file for complete search history.

(56) References Cited

U.S. PATENT DOCUMENTS

| | | | |
|---|---|---|---|
| 5,506,141 A * | 4/1996 | Weinreb et al. | 435/309.1 |
| 6,044,981 A * | 4/2000 | Chu et al. | 210/490 |
| 6,416,164 B1 | 7/2002 | Stearns et al. | |
| 6,509,164 B1 * | 1/2003 | Guirguis | 435/7.2 |
| 6,612,686 B2 | 9/2003 | Mutz et al. | |
| 6,893,836 B2 * | 5/2005 | Mutz et al. | 435/29 |
| 6,932,097 B2 | 8/2005 | Ellson et al. | |
| 7,854,343 B2 * | 12/2010 | Ellson et al. | 220/256.1 |
| 2002/0171037 A1 * | 11/2002 | Ellson et al. | 250/288 |
| 2003/0108450 A1 | 6/2003 | Mainquist et al. | |
| 2005/0176155 A1 * | 8/2005 | Klein et al. | 436/163 |
| 2006/0127883 A1 * | 6/2006 | Mutz et al. | 435/4 |
| 2006/0201948 A1 | 9/2006 | Ellson et al. | |
| 2007/0175897 A1 | 8/2007 | Ellson | |

OTHER PUBLICATIONS

Burfield, D. R.; Smithers, R.H. "Dessicant Efficiency in Solvent Drying. 3. Dipolar Aprotic Solvents." Journal of Organic Chemistry, 1978, 43, pp. 3966-3968.*

* cited by examiner

*Primary Examiner* — Christine T Mui
(74) *Attorney, Agent, or Firm* — Jones Day

(57) ABSTRACT

In an aspect of this invention, a closure for a well plate is provided which has a reservoir. The closure has openings through which acoustic ejection of fluid droplets can take place without removing the closure. The reservoirs in the closure may help to maintain acceptable levels of solvent in the wells of the well plate despite the evaporation which may occur during the course of ejection.

11 Claims, 5 Drawing Sheets

CLOSURES WHICH CONTAIN RESERVOIRS AND ALLOW ACOUSTIC EJECTION

CROSS-REFERENCE TO RELATED APPLICATIONS

This application claims priority to U.S. Provisional Patent Application No. 60/936,586, filed Jun. 20, 2007, which is incorporated by reference herein in its entirety.

TECHNICAL FIELD

This invention relates generally to containers for fluids, and in particular to containers for small quantities of fluid used in chemical and biomedical research and development.

BACKGROUND

In chemical and biomedical research and development, it is common to manipulate large numbers (e.g., thousands) of fluid containers which must be readily and automatably opened and closed, and yet must also be stored for months or years. The need to open and close the containers readily tends to induce the use of relatively poorly sealed containers, whereas the desire to store the containers for months or years tends to make it desirable to achieve tight sealing, for example to avoid evaporation loss and contamination from the outside.

The fluid containers used in chemical and biomedical research are subject to substantial chemical compatibility constraints, for example that they should not be made of materials which would be attacked by the solvents which they are designed to hold. Such constraints will also apply to the closures of such fluid containers. Adhesives are generally not preferred for closure of such fluid containers because of concerns about contamination and nonuniformity arising from adhesive residue left over from one closure to the next.

Examples of fluid containers widely used in chemical and biomedical research and development are well plates and micro tubes. Well plates are commonly used which have 96, 384, and 1536 wells, although other numbers of wells are also in use. The dimensions and other characteristics of well plates have been standardized by the Society for Biomolecular Screening. A common size of well plate is 127.76 by 85.48 by 14.35 mm. Well plates are commonly designed to be stacked on top of each other in storage. Microtubes are commonly used in racks of 96 or 384. These racks of microtubes conform to dimensions similar to the length and width of well plates so they can be handled by similar robotic and automation equipment.

For well plates, a wide variety of lids have been developed. An example of a well plate lid of the prior art is described in U.S. Patent Application Publication No. 2003/0108450. That well plate lid uses the weight of the lid to provide the force which holds the lid to the well plate. The lid is stated to weigh 400 g preferably. A compliant sealing member, preferably of silicone rubber, forms part of the lid and is pressed against the well plate.

There have also been efforts in the art to adapt to evaporation losses. In particular, in some cases the outer wells of a well plate are not used to hold fluids of interest but instead are filled with a volume of the solvent in which those fluids are stored. This solvent in the outer wells has been observed to reduce the rate at which the solvent in the inner wells evaporates. The outer wells are sometimes referred to as "moat wells" when so used.

An alternative means to adapt to evaporation losses is to periodically audit the fluid levels in the reservoirs of the container and to add solvent to those reservoirs as needed. U.S. Pat. No. 6,932,097 describes a convenient automatable way of carrying out the auditing by means of focused acoustic energy. A variety of patent applications to the present assignee describe generally the process of acoustic ejection as employed in chemical and biomedical research, for example U.S. Pat. Nos. 6,416,164 and 6,612,686.

The assignee of the present application has previously filed U.S. Patent Application Publication No. 2006/0201948, which disclosed an approach to dealing with evaporation losses which involves the use of closures which contain reservoirs for additional fluid. Such closures are effective in reducing the loss from evaporation.

U.S. patent application Ser. No. 11/698,004 (U.S. Patent Application Publication No. 2007/0175897), also assigned to the assignee of the present invention, discloses a further approach to dealing with evaporation losses through closure design.

When well plates are supplied with an appropriate closure, they may be stored for considerable periods of time, at least on the order of months, without a damaging loss of fluid in the wells themselves. However, the purpose of storing fluids in well plates is generally to at least occasionally remove fluid for testing purposes. The process of removing fluid is often carried out by means of acoustic ejection.

The removal of fluid from a well plate generally implies removing the well plate's closure. The closure may remain off for a considerable time if fluid is removed from multiple wells in the well plate. It is possible to remove quite small quantities of fluid and use them in tests, for example quantities on the order of picoliters. In such a context it is quite possible that the evaporation losses caused by the removal of the closure to be comparable to or exceed the fluid removed for purposes of experimentation.

There is still a need to provide well plate closures which are further effective in dealing with evaporation losses and in particular losses that occur when fluid samples are removed from a well plate.

SUMMARY OF THE INVENTION

In an aspect of this invention, a closure for a well plate is provided which has a reservoir. The closure has openings through which acoustic ejection of fluid droplets can take place without removing the closure. The reservoirs in the closure may help to maintain acceptable levels of solvent in the wells of the well plate despite the evaporation which may occur during the course of ejection.

In another aspect of this invention, a method of acoustically ejecting a fluid sample comprising a solvent is provided. The fluid sample is placed in a first reservoir. The reservoir is covered with a first closure. The first closure is then removed and replaced with a second closure. Without removing the second closure from the first reservoir, a droplet of fluid is acoustically ejected from the first reservoir.

FIGURES

DETAILED DESCRIPTION OF PREFERRED EMBODIMENTS

Figure 1A:
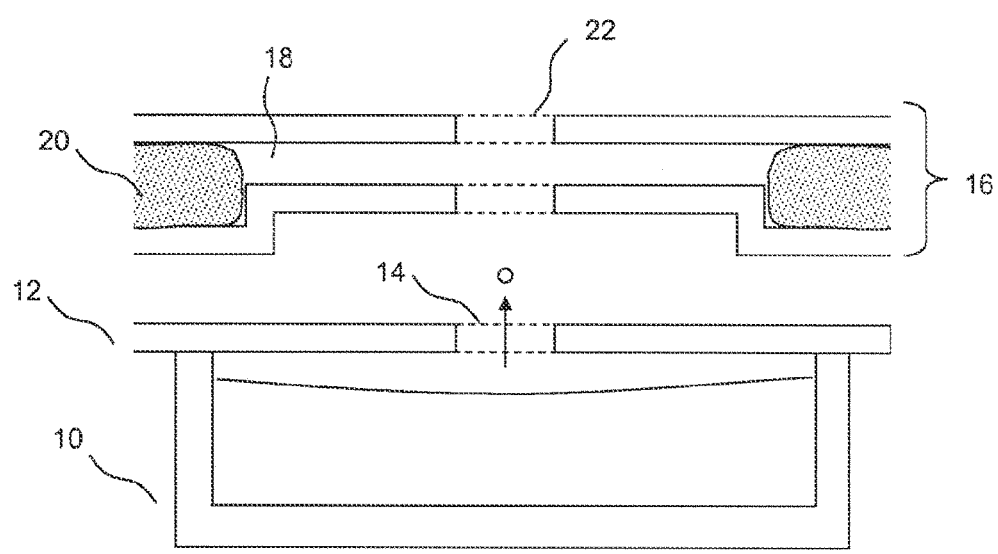
FIGS. 1A-1C depict schematically closures of the invention which have openings which allow droplets to be ejected from a well plate while it is covered with the closure.

Before describing the present invention in detail, it is to be understood that this invention is not limited to specific solvents, materials, or device structures, as such may vary. It is also to be understood that the terminology used herein is for the purpose of describing particular embodiments only, and is not intended to be limiting.

As used in this specification and the appended claims, the singular forms "a," "an," and "the" include both singular and plural referents unless the context clearly dictates otherwise. Thus, for example, reference to "a well" includes a plurality of active ingredients as well as a single active ingredient, reference to "a temperature" includes a plurality of temperatures as well as single temperature, and the like.

In describing and claiming the present invention, the following terminology will be used in accordance with the definitions set out below.

The term "fluid" as used herein refers to matter that is nonsolid, or at least partially gaseous and/or liquid, but not entirely gaseous. A fluid may contain a solid that is minimally, partially, or fully solvated, dispersed, or suspended. Examples of fluids include, without limitation, aqueous liquids (including water per se and salt water) and nonaqueous liquids such as organic solvents and the like. As used herein, the term "fluid" is not synonymous with the term "ink" in that an ink must contain a colorant and may not be gaseous.

"Optional" or "optionally" means that the subsequently described circumstance may or may not occur, so that the description includes instances where the circumstance occurs and instances where it does not.

The term "reservoir" as used herein refers to a receptacle or chamber for containing a fluid. A reservoir may also be a volume of a member within which a fluid is constrained or held.

The term "closure" as used herein refers to a member used to close a container for fluids. It thus encompasses for example lids, stoppers, and caps. A container may be closed with one closure or, in some cases, with multiple closures. Closures normally meet with containers at respective surfaces on each member. The mechanical match of the closure and container at the surfaces where they meet may not be perfect, so that some exchange of vapor between the inside and outside of the container may be possible even with closures in place.

While the principles of the invention are described primarily in relation to well plates, it should be understood that they apply equally to other containers such as storage tubes or microtubes which may contain fluids which are subject to acoustic ejection and for which avoiding evaporation loss is of interest. For convenience, containers which are closed with the closures of the invention may be referred to as "primary members."

In an aspect of this invention, a closure for a well plate is provided which has a reservoir. The closure has openings through which acoustic ejection of fluid droplets can take place without removing the closure. The reservoirs in the closure may help to maintain acceptable levels of solvent in the wells of the well plate despite the evaporation which may occur during the course of ejection.

Solvents used commonly in chemical and biomedical research may be hygroscopic. In particular, it is well known that DMSO is quite hygroscopic and that DMSO solutions will commonly draw humidity from the ambient air. In many circumstances this phenomenon whereby a fluid of interest comprising a hygroscopic solvent draws humidity from the ambient air is undesirable. Hydration of DMSO, for example, may make certain substances less soluble in the DMSO-water mix. A closure which has reservoirs of solvent can help not only to keep evaporation from occurring but also to keep the fluids in the individual wells from drawing undesirable humidity from the ambient air during the process of acoustic ejection.

In a possible practical use of the closures of the invention, a well plate is brought in which has a storage closure. The storage closure is removed from the well plate, for example by means of a robot. A closure of the invention is then placed onto the well plate, and it is then placed inside an apparatus suitable for acoustic ejection of fluid from the well plate. The apparatus may be any type of acoustic ejection device which is able to handle well plates of the appropriate size. Ejection then takes place through the openings in the closure.

The closure may further comprise a thin plate which covers the well plates but contains openings through which acoustic ejection of fluid droplets can take place. These openings in the thin plate are preferably aligned with the ejection openings in the closure.

The openings in the closure are preferably circular. The diameter of the openings may be determined on the basis of two factors: the size of the droplets to be ejected from the well plate and the ease or difficulty of aligning the openings precisely with respect to a reference known to the control of the acoustic ejection apparatus. A lack of alignment may arise for example because of imprecision in the positioning of the closure relative to the well plate, dimensional variation in the closure or the well plate, or inaccuracy in the control's knowledge of the position of the well plate.

Openings of diameter about 1 mm, about 1.5 mm, or about 2 mm are found to be useful. Smaller openings may also prove beneficial and can applied in circumstances where transducer position, droplet trajectories, and the location of the openings in the closure are well controlled. For example, openings that are four times the diameter of the droplet would minimize gas exchange through the opening, yet still enable transfer of the droplet from the well through the opening. With more precise physical alignment, an opening about two times the diameter should suffice, so droplets of 150 microns in diameter could be accommodated by 300 micron openings.

In general each ejection opening in the closures is preferably positioned so that it will lie above the center of a well when the closure is deployed on a well plate. There may be openings for all wells of the well plate or only for some wells, where for example particular wells are used for purposes other than holding fluids which might be acoustically ejected from the well plate.

FIG. 1A schematically depicts an arrangement of closure and well plate as described above. The well 10 holds a quantity of fluid. Above the wells is a thin plate 12 with openings such as 14. Above the plate is the main part 16 of the closure, which comprises a reservoir 18. In the reservoir 18 there may be a substance 20 which absorbs fluid, for example felt.

It may be seen that in FIG. 1 there are at least three zones for vapor, linked by small openings. There is a first zone immediately above each of the wells, there is a zone between the thin plate 12 and the main part 16 of the closure, and there is then a zone within the closure reservoir 18. The third zone may open directly into the acoustic ejection opening 22 as depicted in the figure. The third zone may also open to the second zone through suitable apertures (not shown in the figure).

Figure 1B:
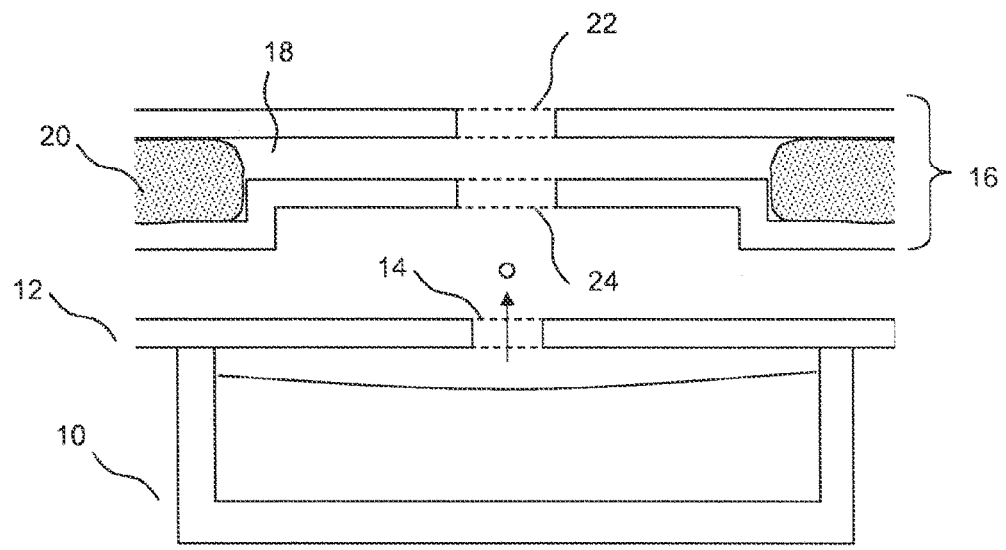
Figure 1C:
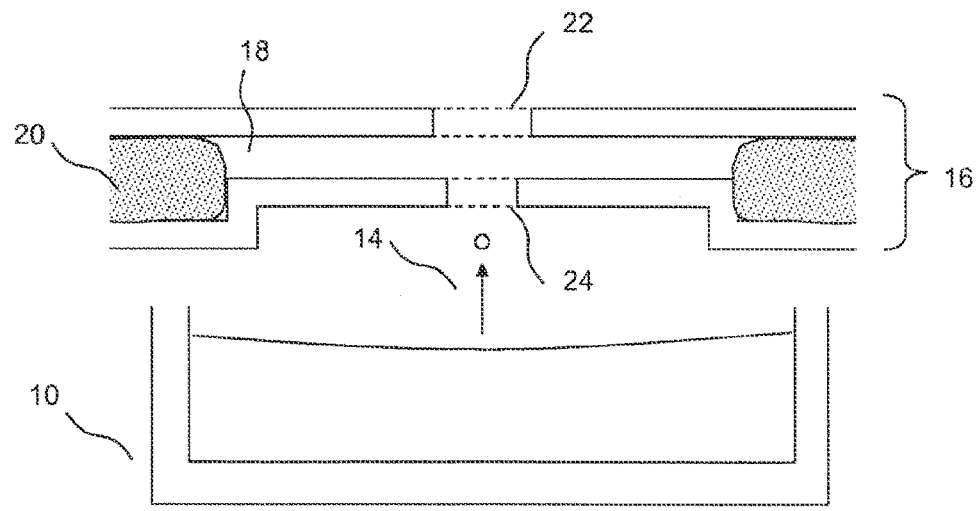

FIGS. 1B and 1C schematically depict other closures of the invention. In FIG. 1B the opening 14 in the thin plate 12 has a smaller diameter than the opening 22 in the main part of the closure. For example, if the alignment of the opening 14 with the well center is more precise than the alignment of 22, then it may be desirable to have 14 be smaller in size than 22. In FIG. 1C there is no thin plate 12, and the opening 22 in the main part of the closure is narrower at the bottom (facing the well plate) than at the top where it opens up to the outside.

Figure 2:
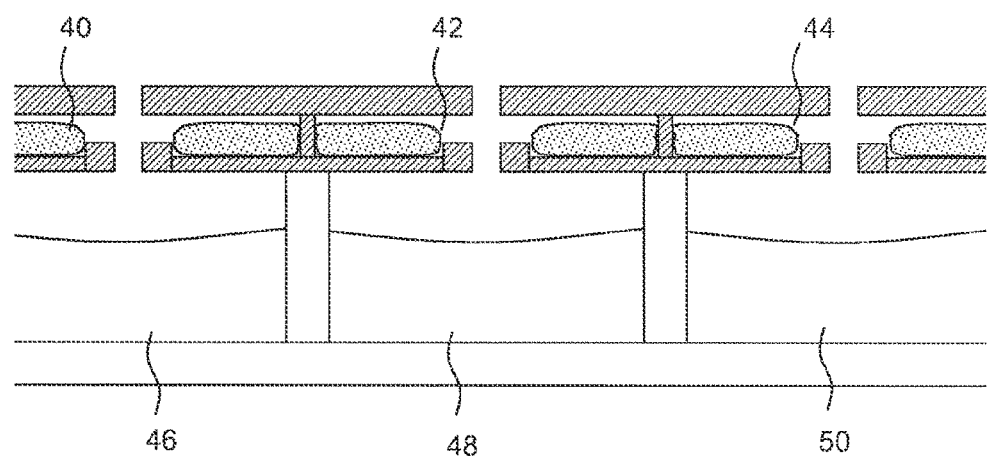
FIG. 2 depicts schematically a further closure of the invention which has multiple reservoirs for different solvents.

FIG. 2 schematically depicts an arrangement of closure and well plate in which there are multiple reservoirs 40, 42, 44 in the closure corresponding to different solvents which are used in different wells 46, 48, 50 of the well plate. In this case there is no thin plate as in FIG. 1; the closure lies directly atop the well plate. This configuration is desirable where different solvents are present in the wells since gas exchange between the closure reservoir and its corresponding well (i.e., 40 and 46) may be greatly enhanced relative to the gas exchange between the adjoining wells (in this example, 46 and 48).

A wide variety of closure structures may be used which contain suitable openings through which the ejected fluid may pass and reservoirs in the closure. In general, reservoirs in the closure provide "sacrificial" fluid to maintain a high vapor pressure in the openings and in the vicinity of the closure on the side facing towards the wells. When there is such a high vapor pressure, molecules of evaporated fluid which escape outside from the vapor above a well will be compensated by molecules of fluid from the reservoirs in the closure which come into the area between wells and closure, preventing evaporation loss of fluid from the reservoirs. As depicted in FIGS. 1A-1C and 2, it is generally preferred that at least one closure reservoir open into each of the ejection openings in the closure, thus feeding the ejection opening with appropriate vapor.

In the invention it is preferred to be able to replenish the fluid in the closure reservoirs periodically. In this way, these reservoirs will always have an adequate supply of fluid, for example of solvent. This periodic replenishment could take place by removing the closure from the container, potentially inverting the closure or otherwise altering its orientation, and using some sort of fluid transport system to dispense fluid into the reservoirs through openings that open into the interior of the container. The fluid transport system could be, for example, manual pipetting, an automatic pipetting system, a tip-based transport system, or an acoustic ejection system. One method would be to dispense fluid directly into each opening in a manner suitable for its transport into the corresponding closure reservoir. Another embodiment would have a deposition of fluid supply the closure reservoir around multiple openings. For example, a lid with 384 openings could have the closure reservoir around the 384 openings supplied with fluid from a single dispense from a 96-tip pipetting system. Each tip would supply fluid to a fluid loading point in the lid that provides a transport means to the vicinity of the four surrounding openings.

Figure 3A:
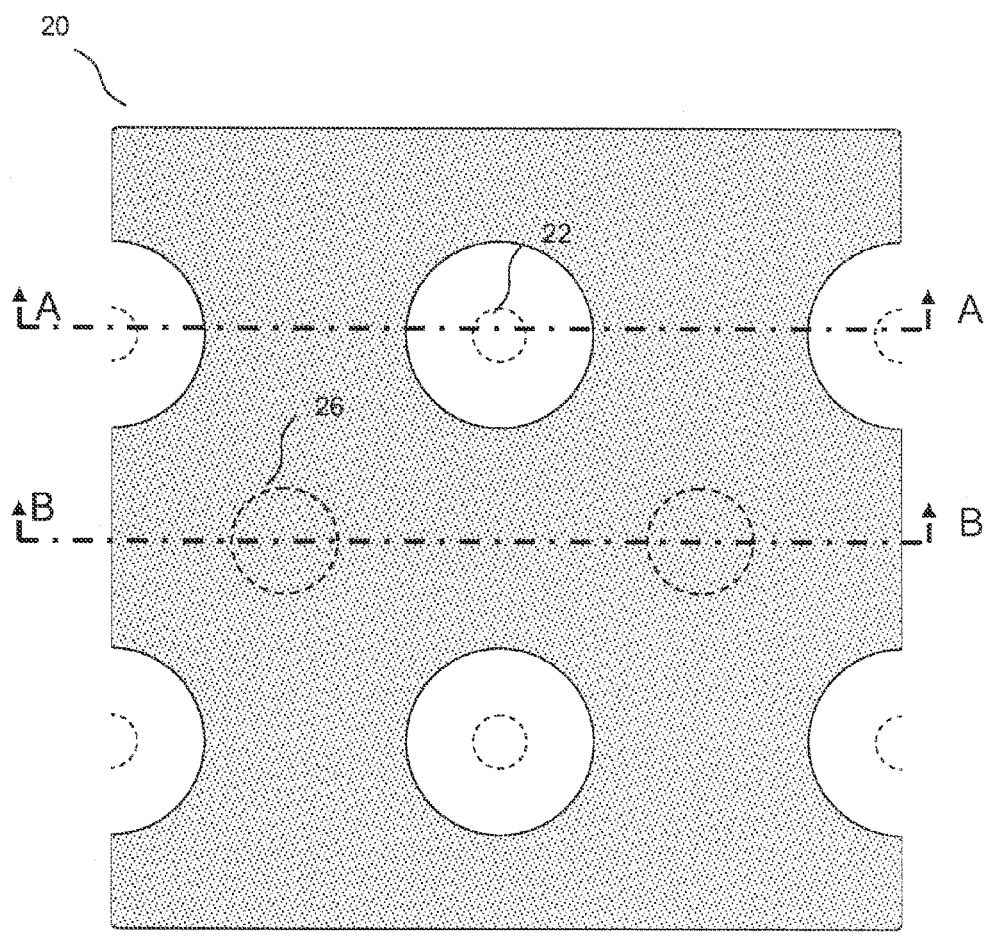
FIGS. 3A-3C depict schematically different views of a closure of the invention arranged to allow easy refilling of the closure reservoirs.
Figure 3B:
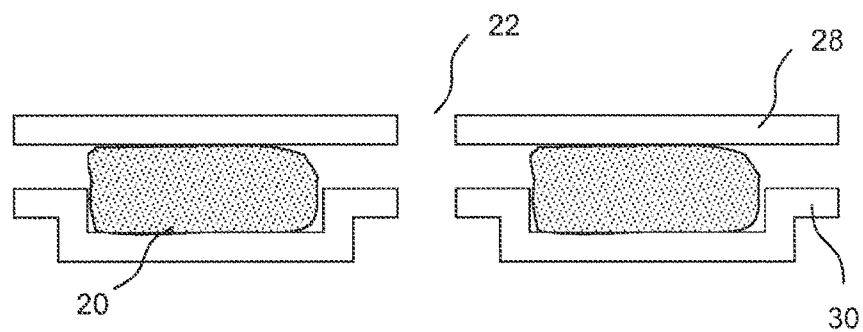
Figure 3C:
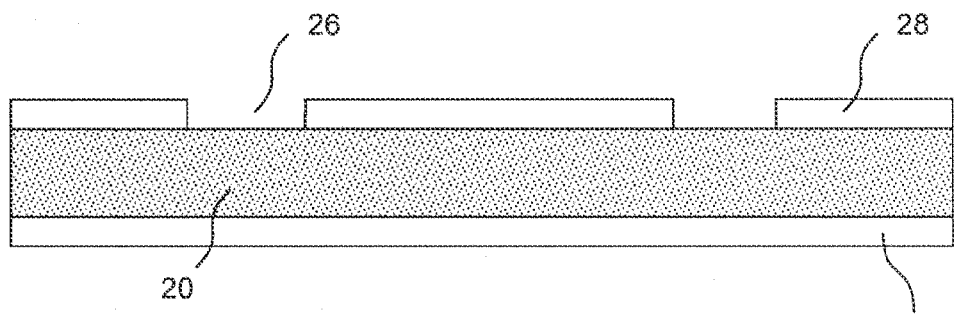

FIGS. 3A-3C depict different views of a possible arrangement of inlets such as 26 in a closure which can be used to replenish the solvent in a closure reservoir. FIG. 3A depicts a top view, while FIG. 3B depicts a section through the line A-A in FIG. 3A, and FIG. 3B depicts a section through the line B-B in FIG. 3A. The closure depicted in FIGS. 3A-3C contains an absorbent material 20 which has openings which enclose the ejection openings in the closure. This absorbent material 20 is placed between an upper portion 28 and a lower portion 30 of the closure. In both the upper portion 28 and lower portion 30 of the closure there are openings for ejection, as may be seen in FIG. 3B. In the upper portion 28 there are also inlets like 26 which serve for loading of fluid from the top of the closure, even when the closure is in place on a well plate. This enables replenishment of the fluid in the closure reservoirs without removing the closure from the well plate. As may be seen, there is one inlet like 26 for each four ejection openings, so that for example if there are 384 wells and 384 ejection openings, the fluid in the closure reservoirs can be replenished from a 96-tip pipetting system.

Similarly, a 384 tip system could supply a 1536-opening lids, and other tip systems could be used to load higher density opening lids.

Similar filling schemes could be designed by one of ordinary skill in the art to enable loading into closure reservoirs like 40, 42 and 44 depicted in FIG. 2. Each closure reservoir would be expected to have at least one loading point like 26 in FIG. 3.

Alternatively, the closure could be designed to have a removable cover or plug, or alternatively a septum plug, for example from a manufacturer such as ABgene (Epsom, United Kingdom). The reservoirs would have one or more openings which open into the interior of the container and another opening which is exposed when the removable cover or plug is removed. The replenishment of the fluid in the reservoirs of the closure could be performed by removing the cover or plug, dispensing fluid, and then replacing the cover or plug. With suitable control of the dispensing process so as to cause a low impact of the added fluid on the mass of fluid already present in the closure reservoirs, and if the openings that open into the interior of the container are sufficiently small, the addition of fluid would not cause any fluid to travel from the reservoirs into the interior of the container. It would be possible, for example, to dispense into reservoirs which do not have openings to the inside of the closure and then to allow the dispensed fluid to travel slowly through suitably sized channels from these reservoirs to other reservoirs which have such openings. The fluid transport system used could again be, for example, an automatic pipetting system, or a tip-based transport system, or an acoustic ejection system.

It could alternatively be practical simply to have permanent openings without a stopper or the like which allow the closure reservoirs to be refilled from the side facing outwards from the well plate.

In the reservoirs of the closures of the invention, it may be desirable to use a material which absorbs a desired solvent or other fluid readily in order to concentrate that fluid where the material is placed. A wide variety of materials which absorb particular solvents well may be used for this purpose. Felt is an exemplary such material. Woven or non-woven fibers, for example, cellulosic fibers, may be used. A variety of foams may also be employed. Foams may include, for example, open-cell foams which have connected voids so they have the ability to hold substantial quantities of liquid and to allow the liquid to move throughout the extent of the foam. Where the solvent is DMSO, a foam that could withstand long-term exposure to DMSO like a polyethylene foams would be preferred. An open-cell polyethylene is OPCELL (described at http://www.chimeng.com.tw/e-opcell.htm) from Chi Meng Industry (Tainan, Taiwan). The use of materials which absorb fluid may help to reduce the chance of non-gaseous transfer of material (e.g., dripping) from the closure reservoirs to the wells.

The fluids of interest in the invention may be any fluid which is being used in research, development, manufacturing, education or other activities requiring fluid handling. In particular, the fluids of interest may contain biological samples such as living organisms or materials derived from such organisms. They may form part of libraries of compounds generated through combinatorial chemistry or otherwise. They may comprise biomolecules or they may comprise synthetic or naturally occurring organic or inorganic molecules.

The reservoirs in the closure may be of a wide variety of shapes. They may be simple indentations, for example of hemispherical or cylindrical shape, arranged around the contact zone on the inside of the closure. A reservoir may simply be a groove arranged around the contact zone on the inside of the closure. Alternatively, it may be a compartment of substantial size spanning much of the closure.

It is preferable that closures be capable of easy opening and closing. In many cases, the closures of the invention will be adapted to being opened and closed by means of robot arms of the type which are commonly used for the manipulation of containers in chemical and biomedical research. Thus, for example, it is preferable if the closure can be put in place by lowering it into position, and then opened simply by lifting it out of position. It is also preferred that the force of the earth's gravity suffice to hold the close in place. It is preferred that the force of the earth's gravity suffice to form the seal between closure and well plate.

Among the considerations which are relevant to the design of the closure the following may be noted.

First, it may be preferred that the total volume of the container with the closure in place be reduced to something close to the minimum volume which is necessary to contain the fluids of interest. The greater the head space inside the container, the greater the amount of fluid that must evaporate to establish a partial pressure approaching the vapor pressure.

Second, to the extent fluid is held in the closure reservoirs through surface forces, it is preferred that these surface forces be sufficient to retain the fluid in its position when the closure is subject to the inevitable forces which accompany the process of closure insertion and removal. Preferably, the process of insertion and removal does not subject the closure to significant forces, but in practice, to the extent this process is carried out by a human or by a general purpose robot arm, there will be some degree of impact of the closure on the well plate, resulting in a more or less sharp deceleration of the closure. It is preferred in particular that certain free surfaces of the fluid retained in the closure reservoirs lie approximately parallel to the direction of the impact force.

Third, while plugs and/or covers for the closure reservoirs are indicated as being desirable, it is also desirable to allow some ability for gases to enter and leave the closure reservoir as for example with a small vent. This ability prevents for example the formation of vacuums in any air space within the closure reservoir. The use of a commercially available septum plug may provide an adequate degree of venting for this purpose.

Fourth, the reservoirs in the closures will generally contain some amount of liquid and a headspace with some amount of gas. Some of the liquid may be free and some of the liquid may be absorbed on an absorbent material such as felt. It is in general desirable that the reservoirs in the closures, and the openings between them and the various zones in which vapor is present, not allow liquid to spill out of the closure reservoirs and onto the well plate. Placing too much liquid in the closure reservoirs when they are refilled could lead to such spilling, as could movement of the closure when it is put on the well plate or removed.

A figure of merit for the closures of the invention is the extent to which they prevent evaporation of a particular solvent (e.g., water, acetonitrile) compared to not having the closure in place. It may be desired that a closure, with its reservoirs filled to design capacity with the solvent, diminish the evaporation rate of the solvent to no more than about 30%, no more than about 10%, or no more than about 3% of what the rate would be without the closure in place.

An alternative figure of merit for the closures of the invention is the percentage of the solvent escaping through the ejection openings and through the seal between closure and well plate which comes from the closure reservoirs. It may be desired, for example, that this percentage be at least about 10%, at least about 25%, or at least about 50%.

Extensive guidance with respect to the formation of a good seal between a closure and a well plate may be found in U.S. Patent Application Publication No. 2006/0201948 and U.S. patent application Ser. No. 11/698,004 (U.S. Patent Application Publication No. 2007/0175897).

The choice of material for the formation of the closures and containers of the invention is constrained also by the need to be compatible with the fluids of interest. Among these, fluids where DMSO by itself or DMSO and water are solvents are of particular interest in chemical and biomedical research. Materials which are compatible with DMSO include cyclic olefin co-polymers (COC), polyethylene (PE), polypropylene (PP), ethylene-propylene rubber (EPR) and polytetrafluoroethylene (PTFE). COC is made by Ticona Engineering Polymers (Summit, N.J.), which is part of Celanese Corporation, and goes by the trade name Topas. One preferred Topas resin is 8007. These materials may advantageously be used to form the closures used in the invention. In general, the closure is preferably readily manufacturable, most preferably by injection molding of a single component or of two or three components subsequently brought together.

The closures of the invention may be manipulated as part of an automated system. An overall laboratory automation system may include, for example, a carousel for holding well plates, a robot arm for moving well plates from one instrument to another, a variety of analytical instruments and reaction chambers, a pin based fluid transfer system, and/or an acoustic ejection system. The overall purposes of the system may include taking quantities of fluids and subjecting them to analyses (including for example the ascertainment of their composition and physical properties), reactions designed to produce particular moieties, and purification steps, all the while potentially keeping track, by computerized or other means, of the origin and destination of each fluid in the system and of the processes and results for each fluid. The system may also be employed to generate for further use objects which contain or are coated with fluids moved by the system. The system may also track the status of each reservoir-containing closure, for example the last time the reservoirs in the closure were filled or the solvent(s) or other fluid(s) in the closure's reservoirs.

The tracking of the origin, destination, processes, and results for each fluid may be performed, for example, by having controllers such as the fluid transport system controller communicate that information to a general purpose computer which stores the information as flat files or in a database. Fluids are conveniently identified by assigning an identifier to each well plate in the system and by tracking what is done to each well in each plate at particular times in a way that allows one to produce an overall history for the contents of each well of each plate. It must be kept in mind in this regard that not all changes in fluids in the system take place as a result of deliberate or planned action; some may be inevitable changes that occur as a result of the passage of time, as for example the absorption of water from the surrounding air or the evaporation of fluids in storage, which the containers and methods of the present invention are concerned with.

In a laboratory automation system it will generally be necessary to integrate equipment from different manufacturers. In this connection the adherence to particular standards may be a desirable feature of a fluid transport system. Certain fluid transport and storage systems which form part of a manufacturing environment may be required to meet further standards relating to manufacturing as well as being able to support overall system conformance with the norms of "Good Manufacturing Practice" (GMP) as understood by the pharmaceutical industry.

It is to be understood that while the invention has been described in conjunction with the preferred specific embodiments thereof, that the foregoing description and the examples that follow are intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

I claim:

1. A method of storing at least one fluid sample comprising a solvent, the method comprising:
    storing at least the fluid sample in at least a well of a well plate;
    covering the well plate with a closure by placing the closure in contact with the well plate such that a surface of the closure meets a surface of the well plate, the closure including at least a first opening defined therethrough and comprising a reservoir holding at least a quantity of the solvent; and
    with the closure remaining in contact with the well plate and without removing the closure from the well plate, acoustically ejecting a droplet of the fluid sample from the well of the well plate through at least the first opening of the closure.

2. The method of claim 1 wherein:
    the reservoir includes a second opening; and
    the covering the well plate with the closure includes allowing an exchange of gas between the reservoir and at least the well of the well plate.

3. The method of claim 1 wherein:
    the covering the well plate with a closure includes:
        forming a seal between the closure and the well plate; and
        allowing an amount of the solvent to escape to the atmosphere through the seal between the closure and the well plate and through at least the first opening;
    wherein at least 10% of the amount of the solvent comes from the quantity of the solvent.

4. A method of acoustically ejecting a droplet of a fluid sample comprising a solvent, the method comprising:
    placing the fluid sample in a first reservoir of a container;
    covering the first reservoir with a first closure by placing the first closure in contact with the container;
    removing the first closure;
    covering the first reservoir with a second closure by placing the second closure in contact with the container such that a surface of the second closure meets a surface of the first reservoir, the second closure including at least a first opening defined therethrough and comprising a second reservoir containing at least a first quantity of the solvent; and
    with the second closure remaining in contact with the container and without removing the second closure from the first reservoir, acoustically ejecting a droplet of the fluid sample from the first reservoir through at least the first opening of the second closure.

5. The method of claim 4 wherein:
    the second reservoir includes a second opening; and
    the covering the first reservoir with the second closure includes allowing an exchange of gas between the second reservoir and at least the first reservoir.

6. The method of claim 4 wherein:
    the covering the first reservoir with a second closure includes:
        forming a seal between the second closure and the container; and
        allowing an amount of the solvent to escape to the atmosphere through the seal between the closure and the well plate and through at least the first opening;
    wherein at least 10% of the amount of the solvent comes from the first quantity of the solvent.

7. The method of claim 4 wherein the first closure comprises a third reservoir containing at least a second quantity of the solvent.

8. A method of storing at least one fluid sample comprising a solvent, the method comprising:
    storing at least the fluid sample in at least a well of a well plate;
    covering the well plate with a closure by placing the closure in contact with the well plate such that a surface of the closure meets a surface of the well plate, the closure including a first portion, a second portion and a reservoir located between the first portion and the second portion, the first portion including at least a first opening defined therethrough, the second portion being opened up to the well with at least a second opening, the reservoir holding at least a quantity of the solvent; and
    with the closure remaining in contact with the well plate and without removing the closure from the well plate, acoustically ejecting a droplet of the fluid sample from the well of the well plate through at least the first opening of the closure and the second opening of the closure;
    wherein:
        the reservoir includes a third opening located between the first portion of the closure and the second portion of the closure; and
        the covering the well plate with the closure includes allowing an exchange of gas between the reservoir and at least the well of the well plate through at least the second opening and the third opening.

9. The method of claim 8, wherein a center of the first opening is aligned so as to be disposed above a center of the well of the well plate.

10. The method of claim 1, wherein a center of the first opening is aligned so as to be disposed above a center of the well of the well plate.

11. The method of claim 4, wherein a center of the first opening is aligned so as to be disposed above a center of the well of the well plate.

* * * * *